United States Patent
Vanlerberghe et al.

[11] 3,972,914
[45] Aug. 3, 1976

[54] NOVEL DERIVATIVES OF GLYCEROL

[75] Inventors: Guy Vanlerberghe, Montjay-la-Tour; Henri Sebag, Paris, both of France

[73] Assignee: L'Oreal, Paris, France

[22] Filed: Mar. 15, 1974

[21] Appl. No.: 451,593

[30] Foreign Application Priority Data
Mar. 22, 1973 Luxembourg .......................... 67263

[52] U.S. Cl................................ 260/496; 260/410.6; 260/410.7
[51] Int. Cl.² ..................... C11C 3/02; C07C 69/30
[58] Field of Search.............. 260/410.6, 410.7, 496

[56] References Cited
UNITED STATES PATENTS

| | | | |
|---|---|---|---|
| 2,131,142 | 9/1938 | Orthner | 260/410.6 |
| 2,192,907 | 3/1940 | Harris | 260/410.6 |
| 2,523,309 | 9/1950 | Kester | 260/410.7 |
| 2,794,037 | 4/1957 | Martin | 260/410.7 |
| 3,067,222 | 12/1962 | Anderson | 260/410.6 |
| 3,242,200 | 3/1966 | Johnsen | 260/410.6 |
| 3,579,548 | 5/1971 | Whyte | 260/410.7 |
| 3,586,528 | 6/1971 | Labana | 260/410.6 |
| 3,632,854 | 1/1972 | Randall | 260/410.6 |

Primary Examiner—Winston A. Douglas
Assistant Examiner—John F. Niebling
Attorney, Agent, or Firm—Cushman, Darby & Cushman

[57] ABSTRACT

Novel bi-substituted derivatives of glycerol of the formula:

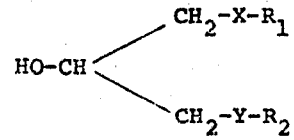

wherein X and Y, which can be the same or different, are either —O— or

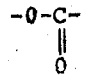

where $R_1$ is a branched alkyl radical having from 5 to 8 carbon atoms, with the number of carbon atoms in the branched portion being 1, 2, or 3, and $R_2$ is a linear alkyl radical having from 11 to 18 carbon atoms. These novel derivatives remain liquid at or below 30°C and are particularly useful in cosmetic compositions.

7 Claims, No Drawings

NOVEL DERIVATIVES OF GLYCEROL

The present invention has for an object novel bi-substituted derivates of glycerol, which have the characteristic of being stable and of being liquid at a temperature lower than or equal to 30°C; the present invention also has for an object the process of preparing these novel derivatives and their utilization in cosmetics.

Certain oily derivatives of glycerol, notably certain glycerides, have already been proposed, for various applications. These compositions, however, are difficult to utilize since they have in their chemical constitution certain unsaturations and, in this way, have the major inconvenience of being oxidizable, thus becoming rancid. On account of these properties, they are not able to be utilized in certain applications, in particular in cosmetic compositions.

The present applicants, after considerable investigations, have come to verify, in a surprising fashion, that it is possible to obtain excellent oils that do not possess the disadvantages of the previously known oils, when certain bi-substituted derivatives of glycerol of a quite particular chemical constitution are utilized.

The novel bi-substituted derivatives of glycerol according to the present invention are either diethers, diesters, or ether-esters of glycerol.

As indicated previously, they show the peculiarity of being liquid at a temperature below or equal to 30°C. This property permits their utilization in different areas and in particular in the area of cosmetics.

These novel bi-substituted derivatives of glycerol exhibit, moreover, the advantage of having good solubilizing properties and an excellent solubility in the usual solvents, as well as in the numerous oils frequently utilized, notably in cosmetics.

Finally these novel derivatives permit a better spreading on water, a property particularly interesting for certain applications, especially for the formulation of bath oils.

Taking into account the general effect of these properties of the novel bi-substituted derivatives of glycerol according to the present invention, the latter are able to advantageously replace the natural oils up until now utilized, especially in cosmetics.

The present invention has therefore for an object novel bi-substituted derivatives of glycerol, which are liquid at a temperature lower or equal to 30°C, as well as mixtures of these novel derivatives, these novel derivatives being characterized by the fact that they correspond to the following general formula I:

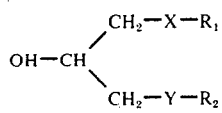
(I)

in which:
X and Y, which are identical or different, represent: either —O— or

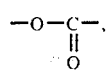

where
$R_1$ represents a branched alkyl radical having from 5 to 8 carbon atoms, the number of carbon in the branch being 1, 2 or 3,
and $R_2$ represents a linear alkyl radical having from 11 to 18 carbon atoms.

As can be ascertained from the general formula mentioned above, these novel derivatives of glycerol are asymmetric compounds, the radicals $R_1$ and $R_2$ being different in the same molecule.

In effect, one can state that in order to obtain advantageous properties, and notably a liquid state at a temperature less or equal to 30°C, it is important that at least one of the radicals have a branched aliphatic chain comprising from 5 to 8 carbon atoms.

According to the present invention the radical $R_1$ can be a radical such as one of those represented below, without, however, this list being limiting:

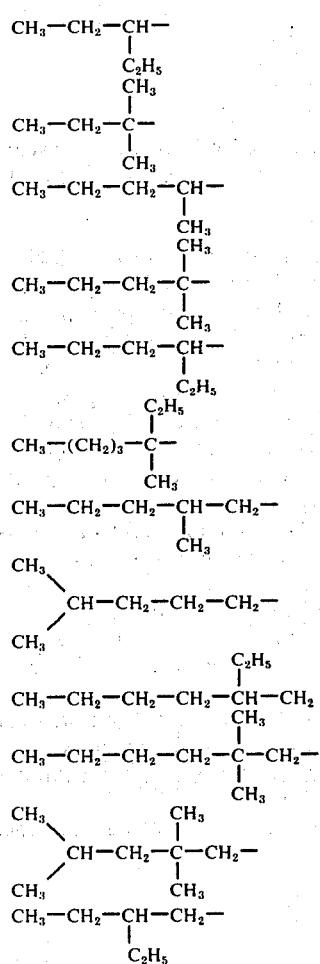

The substituent $R_1$ can be represented especially by
(a) either a radical of the formula:

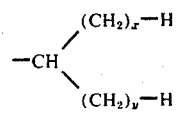

$x$ being a whole number equal to 1, 2 3, and $y$ being a whole number which can vary from 2 to 6, such that the sum $(x+y)$ is either less than or equal to 7 and greater or equal to 4; or (b) a radical of the formula:

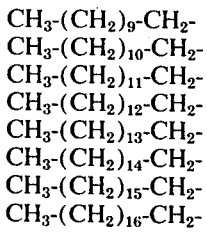

$x$ being defined as above, and $z$ being a whole number that can vary from 2 to 5, such that the sum $(x+z)$ is less or equal to 6 and greater or equal to 3.

According to the present invention, the radical $R_2$ can be a radical such as those represented below:

$CH_3$-$(CH_2)_9$-$CH_2$-
$CH_3$-$(CH_2)_{10}$-$CH_2$-
$CH_3$-$(CH_2)_{11}$-$CH_2$-
$CH_3$-$(CH_2)_{12}$-$CH_2$-
$CH_3$-$(CH_2)_{13}$-$CH_2$-
$CH_3$-$(CH_2)_{14}$-$CH_2$-
$CH_3$-$(CH_2)_{15}$-$CH_2$-
$CH_3$-$(CH_2)_{16}$-$CH_2$-

Among the bi-substituted derivatives of glycerol of formula (I) according to the invention, one is able to cite in particular:

dodecyloxy-1 (ethyl-2)-hexyloxy-3 propanol-2;
hexadecyloxy-1 (ethyl-2)-hexyloxy-3 propanol-2;
octodecyloxy-1 (ethyl-2)-hexyloxy-3-propanol-2;
dodecanoyloxy-1 (ethyl-2)-hexyloxy-3 propanol-2;
hexadecanoyloxy-1 (ethyl-2)-hexyloxy-3 propanol-2;
octadecanoyloxy-1 (ethyl-2)-hexyloxy-3 propanol-2;
dodecyloxy-1 (ethyl-2)-hexanoyloxy-3 propanol-2;
octadecyloxy-1 (ethyl-2)-hexanoyloxy-3 propanol-2;
hexadecanoyloxy-1 (ethyl-2)-hexanoyloxy-3 propanol-2;
octadecyloxy-1 (ethyl-2)-butanoyloxy-3 propanol-2;
tetradecyloxy-1 (ethyl-2)-hexanoyloxy-3 propanol-2;

as well as mixtures of these derivatives.

The present invention also has for an object, a process of preparing the novel derivatives of glycerin of formula (I).

The novel derivatives of glycerin of formula (I) are prepared, preferably, by a process principally characterized in that an acid or alcohol III is reacted with a glycidyl ester or ether II.

The reaction scheme can be represented in the following manner;

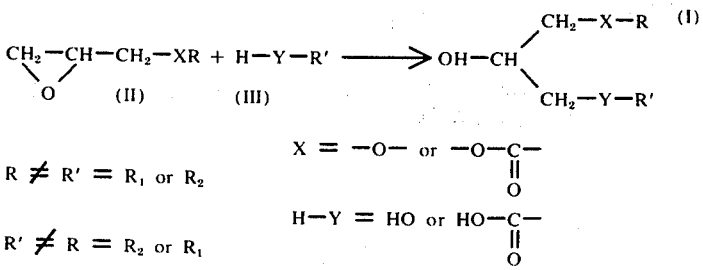

The glycidyl ethers of formula (II), X representing an atom of oxygen, and the glycidyl esters of formula II, X representing the group

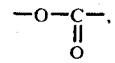

are prepared, for example, by epoxidation of allylic ethers or esters with a peracetic acid according to the following reaction scheme:

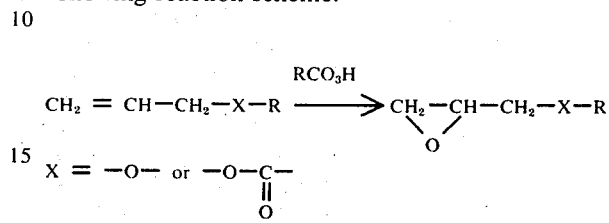

Nevertheless, other methods of obtaining these glycidyl derivatives can be employed, such as by the action of alkaline agents on halohydrins.

In the process according to the present invention, the quantity of alcohol of formula (III) (case where H-Y represents HO-), or the quantity of acid of formula (III) (case where H-Y represents

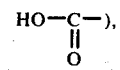

can be varied in large proportions, with regard to the quantity of glycidyl derivatives of formula (II), notably from the stoichiometric quantity to ten times this amount.

One utilizes preferably an excess, when one reacts an alcohol with the glycidyl derivatives in order to reduce, if not avoid, the secondary reactions that can intervene on the secondary alcohol after opening of the oxiran ring.

When according to the present invention one reacts an acid or an alcohol with the glycidyl esters or ethers of formula (II), the reaction is generally carried out without a solvent, at a temperature from about of 60° to 150°C in the presence of basic catalysts in the molar proportions of 0.5 to 5%, with regard to the glycidyl ester or ether.

The reaction temperature can vary from 1 to 14 hours.

The basic catalysts utilized in order to realize the opening of the oxiran ring can be tertiary amines, such as for example triethylamine or N,N,N',N'-tetramethyl-1,3-butane diamine, or an alkali metal alcoholate such as sodium methylate or ethylate.

In the case of the reaction of an alcohol with a glycidyl ether or ester, the reaction can also be realized in the presence of an acid catalyst, such as the Lewis acids, as for example $BF_3$ or $SnCl_4$.

Nevertheless, in this case the opening of the oxiran ring is not totally in one direction, and there forms as a consequence a certain proportion of derivatives of glycerol bi-substituted in the 1,2 positions.

The invention has also for its object the products obtained by the process described above, which contain a certain proportion of derivatives of glycerol bi-substituted in positions 1 to 2, as well as their utilization as cosmetic oils in the same manner as for the compounds of formula I.

nevertheless prejudicial presence of these secondary products, the content of which it is difficult to determine even approximately, is not nevertheless prejudicial to the properties of the glyceryl derivatives according to the present invention. These secondary products, in particular, do not have any marked influence on the fluidity.

In order to isolate the glycerol derivatives according to the invention, from the reaction mixture one proceeds initially with one or more water washes after neutralization with a base when one reacts with an acid, then after drying under reduced pressure, one is able, if one desires, to proceed with a molecular distillation under a vacuum of the order of $10^{-3}$ to $10^{-5}$ mm/Hg.

The products obtained exist, at an ambient temperature of 18°–25°C, in the form of colorless and odorless oils having a viscosity at 25°C between about 10 cps to 100 cps (viscometer with coaxial cylinders).

Among the various alcohols that one is able to react with the glycidyl ethers or esters, one in particular is able to cite: dodecanol, tetradecanol, hexadecanol, octadecanol, ethyl-2 butanol-1, methyl-2 or methyl-4 pentanol-1, 1 ethyl-2 hexanol, dimethyl-2,2 hexanol-1, trimethyl-2,2,4 pentanol-1 and ethyl-2 butanol.

Among the different acids that one is also able to react with the glycidyl ethers and esters, one can particularly cite: lauric acid, myristic acid, palmitic acid, stearic acid, ethyl-2 butanoic acid, dimethyl-2,2 butanoic acid, methyl-2 pentanoic acid, dimethyl-2,2 valeric acid, ethyl-2 hexanoic acid, and ethyl-2 methyl-2 caproic acid.

The present invention also has for an object the utilization of the bi-substituted derivatives of glycerol, such as those described above, or their mixtures, as cosmetic oils in the formulation of cosmetic compositions.

The present invention has especially for an object the utilization as cosmetic oils of the bi-substituted derivatives of glycerol obtained according to one of the processes of preparation mentioned above, and in particular the utilization of the derivatives described below in examples 1 to 11.

As is already known, oils, synthetic or natural, enter into the formulation of numerous cosmetic formulations.

When one examines the different possible formulations, one observes in effect that practically all contain, to a degree more or less, at least one oil.

The novel derivatives of glycerol according to the present invention have the characteristic of being liquids at a temperature less than or equal to 30°C and possess excellent cosmetic properties, and it has been discovered that they constitute compositions of choice utilizable as cosmetic oils for the realization of numerous formulations, among which one can cite, without this enumeration being limiting, milks, creams, emulsions, various makeup products, such as lipsticks and rouges, shampoos, lacs, antiperspirant compositions and deodorants, depilatory products, bath compositions, anti-sunburn products, capillary products, and the like.

As has been indicated previously, the bisubstituted derivatives of glycerol according to the invention possess all of the properties generally required for cosmetic oils, but certain of these properties are in many cases clearly superior to those of cosmetic oils currently utilized.

In particular, they can be applied very easily on the skin, penetrating it and leaving on the surface a non-greasy film with hydrophobic power; they have excellent solubilizing properties which permits them to be utilized as vehicles for various organic compositions, such as perfumes, dyes, active products and the like; finally they have very good emollient properties that is to say principally softening and lubricating.

Taking into account these properties and the various advantages, one thus conceives that the derivatives of glycerol according to the invention find a large application in cosmetics.

The present invention also has for an object cosmetic compositions based on the bi-substituted glycerol derivatives described above, and their mixtures.

The cosmetic compositions according to the invention are especially those based on the bi-substituted derivatives of glycerol obtained according to one of the processes of preparation described above, and in particular, the compositions realized on the basis of the derivatives described below in examples 1 to 11.

The derivatives of glycerol according to the invention are in general utilized in the compositions of the invention at a concentration which can be varied over large proportions, being given that it depends upon the type of formulation; nevertheless it generally can vary between about 0.5 and 60%, notably between 1 and 50%, and preferably from 5 to 50% based upon the total weight of the cosmetic composition.

The derivatives are able to be utilized either alone or in mixture with other natural or synthetic oils, or even as a mixture with waxes.

The compositions according to the invention contain, besides the bi-substituted derivatives of glycerol, the active ingredients or excipients usually utilized in the formulations mentioned above, such as surface-active agents, coloring materials, perfumes, astringents, ultra-violet absorbing products, preservatives, emulsifiers, water, alcohols, and the like.

These compositions are prepared according to the usual methods and are put in a form suitable for utilization. They constitute thus especially lipsticks, deodorant sticks, mascara sticks, tubes or jars of creams (creams for the face, hands, body, depilation creams, anti-sunburn creams, makeup-removal creams, complexion creams, shampooing creams), bottles of fluid composition such as complexion fluids, make-up removal milks, anti-sunburn milks, bath oils, shampoos, or aerosol containers containing liquid compositions or lathers and the like.

In order to better understand the invention, there is given now as illustration, without any limiting character, some examples of the preparation of the novel bi-substituted derivatives of glycerol according to the invention, as well as various examples of cosmetic compositions.

EXAMPLE 1

Preparation of a Compound of the Following Formula:

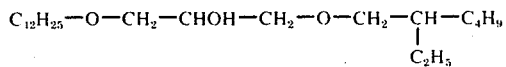

To 744 grams of dodecanol (4 moles), there is added at 70°C under nitrogen, 5.5 g of sodium methylate in methanol (5.75 meq/g), then the mixture is heated at 140°–150°C to eliminate the methanol.

After 3 hours 186 grams of the ethyl-2 hexyl ether of glycidol (1 mole) is added and the temperature is maintained with stirring for 5 hours after the addition. One follows the reaction by the disappearance of the epoxide group.

One washes with 3 × 250 ml of water at 90°C after having neutralized with some drops of hydrochloric acid. One dries by heating under partial vacuum. One distills the excess alcohol (0.05 mm/95°C), the the reaction product at 150°–160°C under a partial vacuum of 0.05 to 0.1 mm of Hg.

One thus obtains 233 grams of a product which has the appearance of a colorless and odorless oil whose temperature of declining liquifaction is below 0°C.

Hydroxyl index: 2.64 – 2.65 meq/g
$n_d^{30} = 1.4450$
viscosity at 25°C = 21 cps

EXAMPLE 2

Preparation of a Compound of the Following Formula:

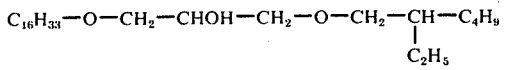

To 485 g of cetyl alcohol (2 moles), is added at 70°C 12.5 g of sodium methylate in methanol (4.75 meq/g) under a nitrogen atmosphere. The temperature is raised to 140°–150°C to eliminate the methanol then 186 grams of the ethyl-2 hexyl ether of glycidol (1 mole) is added dropwise. Duration of the addition: 3 hours. The temperature is kept at 140°–150°C for an additional 4 hours.

The end of the reaction is checked by the disappearance of the epoxide function.

After neutralization with several drops of hydrochloric acid, one washes three times with 250 mls of water at 90°C.

One dries afterwards by heating under vacuum and one distills the excess cetyl alcohol (118°–132°C under a pressure of 0.05 mm of Hg).

The product is then purified by molecular distillation at 160°C under $10^{-3}$ mm of Hg after a first passage at 110°C in order to eliminate volatile products.

There is obtained a colorless and odorless oil having the following characteristics:
Temperature of declining liquefaction: 11°–13°C
Hydroxyl index: 2.25 – 2.27 meq/g
$n_d^{30} = 1.4485$
Viscosity: 33 cps at 25°C.

EXAMPLE 3

Preparation of a Compound of the Following Formula:

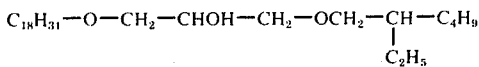

To 260 g of ethyl-2 hexanol (2 moles) is added 1 ml of the acetic complex of boron trifluoride (36% in acetic acid), then at 75°C, 150g of the stearyl ether of glycidol (0.4 equivalents of the epoxide group) is added drop-wise. The addition takes about 2 hours.

One maintains the reaction medium at 75°–80° for an additional 30 minutes after the end of the addition. One confirms that the reaction is ended by the almost total disappearance of the epoxide fraction.

The product obtained is then washed two times with 100 ml of water which is at a temperature of 80°–85°C. One first dehydrates, then the alcohol is eliminated by distillation under vacuum.

By molecular distillation at a temperature of 165°C 40 × $10^{-3}$ mm Hg, one obtains a colorless and odorless oil characterized by the following:

Hydroxyl index: 2.10 – 2.14 meq/g
Temperature of declining liquefaction: 18°–20°C
Refractive index at 30°C: $n_D^{30} = 1.4498$
Viscosity at 25°C: 38 cps This product contains as a mixture a certain quantity of 1,2- diethers.

EXAMPLE 4

Preparation of the Compound of the Following Formula:

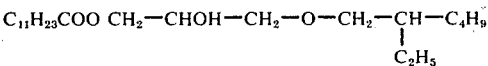

In a 500 ml round-bottom flask, one heats until melting 100.5 grams of lauric acid (0.5 equivalents of acid) under a nitrogen atmosphere and one adds 4.5 g of sodium methylate in methanol. One then heats at 125°C in order to eliminate the methanol and adds over 15 minutes 88.5 g (0.47 moles) of the ethyl-2 hexyl ether of glycidol. One maintains this temperature for 7 hours and follows the reaction by the disappearance of the acid function. At the end of 7 hours the reaction yield is about 95%. One neutralizes the remaining acid with sodium methylate and washes with 3 × 100 ml of water at 80°C. In order to improve the decantation, one adds 25 ml of isopropyl alcohol.

The organic phase is then dried at 100°C under 15 mm of Hg.

The product is purified by molecular distillation at a temperature at 135°C. One obtains a colorless and odorless oil whose declining temperature of liquifaction is below 0°C.

Hydroxyl index: 2.52 – 2.53 meq/g
Saponification index 2.5 meq/g
$n_D^{30} = 1.4473$
Viscosity at 25°C: 31 cps

EXAMPLE 5

Preparation of the Compound of the Following Formula:

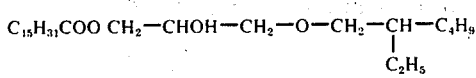

To 254 g of fused palmitic acid (1 mole) one adds 4 g of sodium methylate in methanol under an atmosphere of nitrogen. One heats to a temperature of 110°–120°C to eliminate the methanol, then one adds drop-wise 182 g of the ethyl-2 hexyl ether of glycidol (0.98 moles) over 30 minutes. One then heats for 10 hours at 120°C, at the end of which time one obtains a reaction yield of 98%.

One neutralizes the excess acid with sodium methylate and washes two times with 250 ml of water at 85°C. During the course of the first washing, one adds agains 25 to 30 ml of isopropyl alcohol in order to improve the decantation.

After eliminating volatile material, the product is purified by molecular distillation under $10^{-3}$ mm of Hg and at a temperature of 170°C. One thus obtains a colorless and odorless oil having the following characteristics:

Hydroxyl index 2.18 – 2.20 meq/g
Saponification index 2.1 meq/g
Declining liquification temperature 14°C
Refractive index at 30°C $n_D^{30} = 1.4502$
Viscosity at 25°C: 47 cps

EXAMPLE 6

Preparation of the Compound of the Following Formula:

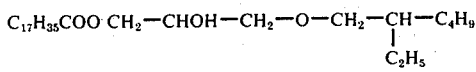

To 548 g of fused stearic acid (2 equivalents of acid), one adds under a nitrogen atmosphere 10.5 g of a methanolic solution of sodium methylate. One heats at 125°C to eliminate the methanol and then one adds dropwise over 2 hours 360 g (1.94 moles) of the ethyl-2 hexyl ether of glycidol.

After 4 hours of continued heating at 125°–130°C one achieves a reaction of 97%. One neutralizes the excess acid with sodium methylate and washes three times with 300 ml of water at 90°C. One adds, if necessary, 20–30 ml of isopropyl alcohol in order to assist the decantation.

As in the preceeding examples, the product is purified by molecular distillation under $10^{-3}$ mm of Hg at a temperature of 195°C.

One obtains a very slightly colored oil whose temperature of declining liquifaction is 22°C.

Hydroxyl index: 1.98 meq/g
Saponification index: 2.2 meq/g
$n_D^{30} = 1.4502$
Viscosity at 25°C: 43 cps

EXAMPLE 7

Preparation of The Compound of the Following Formula:

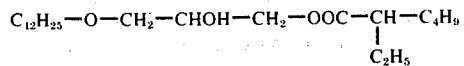

To 29.3 grams of ethyl-2 hexanoic acid (0.2 equivalents of acid) one adds under nitrogen 4 meq of sodium methylate in methanol (0.77 g). One heats at 130°–140°C and adds drop-wise over an hour 51.5 g of the dodecyl ether of glycidol (0.2 equivalents of epoxide). After 8 hours and 30 minutes of heating at 130°–140°C, the reaction yield is 97%.

After washing, as in the preceding examples, one purifies by molecular distillation at a temperature of 125°C.

One thus obtains a colorless and odorless oil.
Temperature of declining liquifaction below 0°C.
$n_D^{30} = 1.4461$
Viscosity 25°C: 35 cps
Hydroxyl index: 2.57 meq/g
Saponification index: 2.6 meq/g

EXAMPLE 8

Preparation of the Compound of the Following Formula:

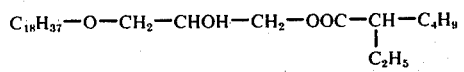

To 45 grams of ethyl-2 hexanoic acid (0.305 equivalents of acid), one adds 1.1 g of a methanolic solution of sodium methylate (6 meq). One heats at 125°C then one adds over 45 minutes 107 g of the stearyl ether of glycidol (0.3 equivalents in epoxide). After 11 hours of heating at 125°C, the reaction yield is 96%.

One neutralizes the non-reacted acid with sodium methylate and washes three times with 200 ml of water at 85°–90°C.

One dehydrates by heating under partial vacuum with a water pump and finishes by a molecular distillation (at a temperature of 160°C).

One obtains a colorless and odorless white product whose declining temperature is 23°C.

Hydroxyl index: 2.16 meq/g
Saponification index: 2.12 meq/g
Viscosity (25°C): 57 cps

EXAMPLE 9

Preparation of the Compound of the Following Formula:

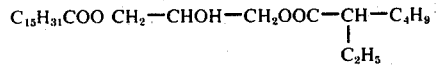

To 21.3 gram of ethyl-2 hexanoic acid (0.145 equivalents of acid) one adds 0.5 grams of a methanolic solution of sodium methylate, then at 135°–140°C over 30 minutes, 50 g of glycidyl hexadecanoate (0.142 equivalents in epoxide).

After 2 hours and 30 minutes of heating at the same temperature, the yield of the reaction is 97%. As previously, the excess acid is neutralized and the organic phase is washed with hot water.

One finishes by purification by molecular distillation at a temperature of 170°C under $10^{-3}$ mm Hg.

One thus obtains a colorless and odorless oil.
Temperature of declining liquifaction: 9°–10°C
Hydroxyl index: 2.2 meq/g
Saponification index: 4 meq/g
$n_D^{30} = 1.4503$
Viscosity (25°C): 71 cps.

EXAMPLE 10

Preparation of the Compound of the Following Formula:

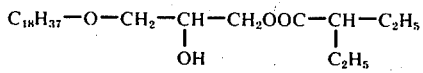

To 25 grams of ethyl-2 butyric acid (0.21 mole) one adds 1.1 grams of a methanolic solution of sodium methylate and one heats under a stream of nitrogen up to a temperature of 130°C.

One then adds drop-wise 75 grams of the stearyl ether of glycidol (0.21 moles) over 30 minutes and maintains the heating for 5 hours. One neutralizes the remaining acid and washes with 3 × 150 ml of water.

One dries under partial pressure and purifies by molecular distillation at a temperature of 160°C. One thus obtains a colorless and odorless product whose temperature of declining liquifaction is 25°–26°C.

Hydroxyl index: 2.27 meq/g
saponification index: 2.25 meq/g
$n_D^{30} = 1.4498$
Viscosity (30°C): 39 cps.

EXAMPLE 11

Preparation of the Compound of the Following Formula:

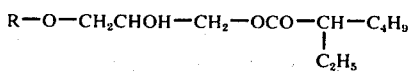

R : mixture $C_{12}H_{25}$ and $C_{14}H_{29}$

To 58.6 grams of ethyl-2 hexanoic acid one adds 0.44 grams of sodium methylate in the form of a powder. One heats to 130°C under a nitrogen atmosphere and adds over 35 minutes 117.6 g of a mixture of the dodecyl and the tetracedyl ether of glycidol available commercially from Proctor and Gamble under the name "Epoxyde 8" (about 75% of the dodecyl - 25% of the tetradecyl). One keeps the temperature between 130° and 140°C for 9 to 10 hours.

One finally washes with 3 × 250 ml of water after having neutralized the nonreacted acid with an aqueous solution of sodium hydroxide.

The product obtained is dehydrated by heating under partial reduced pressure and then purified by molecular distillation after a first purification at 100°C in order to eliminate volatile material. The produce is distilled at a temperature of 145°C under a vacuum of $10^{-3}$ mm of Hg.

One thus obtains a colorless oil having the following characteristics:
Temperature of declining liquifaction below −10°C
Viscosity at 25°C: 35 cps
$n_D^{30} = 1.44732$ Saponification index: 2.44 – 2.49 meq/g
Hydroxyl index: 2.41 – 2.42 meq/g.

EXAMPLES OF COSMETIC COMPOSITIONS

Example I

A day cream is prepared by mixing the following ingredients:

| | | |
|---|---|---|
| Stearyl Alcohol oxyethylene (10 OE) | 4 | g |
| Glycol Distearate | 1 | g |
| Cetyl Alcohol | 1.2 | g |
| Glycerol Stearate | 2 | g |
| Stearic acid | 0.5 | g |
| Compound Obtained in Ex 5 | 16 | g |
| Carboxy vinyl polymer sold by the Goodrich Company under the name Carbopol 940 | 0.3 | g |
| Triethanolamine | 0.3 | g |
| Methyl p-hydroxy benzoate | 0.3 | g |
| Perfume | 0.3 | g |
| Water quantity sufficient for | 100 | g |

Example II

A make-up removal milk is prepared by mixing the following ingredients:

| | | |
|---|---|---|
| Compound obtained in Ex 7 | 5 | g |
| Vaseline Oil | 5 | g |
| Isopropyl Palmitate | 5 | g |
| Stearic Acid | 1.4 | g |
| Triethanolamine | 0.7 | g |
| Glycerol Stearate | 2 | g |
| Carboxy vinyl Polymer sold by the Goodrich Company under the name Carbopol 941 | 0.25 | g |
| Methyl p-hydroxy benzoate | 0.3 | g |
| Water quantity sufficient for | 100 | g |

Example III

An emulsifiable bath oil is prepared by mixing the following ingredients:

| | | |
|---|---|---|
| Compound obtained in Ex 3 | 25 | g |
| Polyglyceryl Isostearate | 10 | g |
| Sweet Almond Oil | 20 | g |
| Isopropyl Palmitate | 10 | g |
| Stearyl Alcohol Oxyethylene (10 OE) | 30 | g |
| 2 and 3 -tert-butyl hydroxy-4 anisole | 0.1 | g |
| Perfume Colorant | 4.9 | g |

After mixing, the mixture is heated to a temperature below 50°C until complete homogenization.

Example IV

Night Cream

A cream is prepared according to the following formula:

| | | |
|---|---|---|
| Tween 60 Polysorbate (Atlas Chemical) | 2 | g |
| Cetyl Alcohol | 1.5 | g |
| Compound of Example 6 | 40 | g |
| Stearyl Alcohol | 1.5 | g |
| Carbopol 940 | 0.4 | g |
| Triethanolamine | 0.4 | g |
| Methyl p-hydroxy benzoate | 0.3 | g |
| Demineralized Sterile water | 53.9 | g |
| | 100.0 | g | p

Example V

Make-Up Removal Cream

A cream is prepared according to the following formula:

| Stearic acid | 10.0 g |
|---|---|
| Triethanolamine | 2.5 g |
| Cetyl Alcohol | 2.5 g |
| Compound of Example 8 | 35.0 g |
| Methyl p-hydroxy benzoate | 0.3 g |
| Demineralized sterile water | 49.7 g |
| | 100.0 g |

Example VI

Body Cream

A cream is prepared according to the following formula:

| Stearic acid | 3.0 g |
|---|---|
| Triethanolamine | 1.7 g |
| Cetyl Alcohol | 0.5 g |
| Carbopol 941 | 0.2 g |
| Methyl p-hydroxy benzoate | 0.3 g |
| Compound of Example 11 | 12.0 g |
| Demineralized Sterile Water | 82.3 g |
| | 100.0 g |

Example VII

Day Cream

A cream is prepared according to the following formula:

| Brij 56 Ether of Fatty Polyethoxyl alcohol (Atlas Chemical) | 2.0 g |
|---|---|
| Cetyl Alcohol | 1.5 g |
| Compound of Example 1 | 24.0 g |
| Carbopol 941 | 0.4 g |
| Triethanolamine | 0.4 g |
| Methyl p-hydroxy benzoate | 0.3 g |
| Sterile demineralized water | 71.4 g |
| | 100.0 g |

Example VIII

Eyelid Make-Up Stick

A stick is prepared from the following formula:

| Ozokerite | 35.00 g |
|---|---|
| Vaseline | 6.00 g |
| Lanolin | 12.00 g |
| Compound of Example 1 | 46.95 g |
| B.H.T. (2,6-di-tert-butyl-p-cresol) | 0.05 g |
| | 100.00 g |

Example IX

Rouge with Fatty Base

A rouge is prepared according to the following formula:

| Isopropyl Stearate | 29.0 g |
|---|---|
| Compound of Example 3 | 34.0 g |
| Glycerol Monostearate | 30.0 g |
| Kaolin | 2.0 g |
| Titanium dioxide | 3.5 g |
| Iron oxide | 1.5 g |
| | 100.0 g |

Example X

Complexion Cream

A complexion base is prepared according to the following formula:

| Stearate of polyethylene glycol | 0.9 g |
|---|---|
| Stearate of glycerol | 5.0 g |
| Vaseline Oil | 8.0 g |
| Compound of Example 3 | 13.0 g |
| Isopropyl Lanolate | 6.0 g |
| Cetyl Alcohol | 2.2 g |
| Methyl p-hydroxy benzoate | 0.3 g |
| Demineralized water, sufficient quantity for | 100.0 g |
| | 100.0 g |

Titanium dioxide  
Iron Oxide  } sufficient quantity according to the desired shades  
and Kaolin

Example XI

Complexion Fluid

A tinting base is prepared according to the following formula:

| Stearic Acid | 4.6 g |
|---|---|
| Vaseline Oil | 5.0 g |
| Cetyl Alcohol | 0.5 g |
| Compound of Example 11 | 18.0 g |
| Triethanolamine | 1.8 g |
| Bentonite | 2.0 g |
| Methyl p-hydroxy benzoate | 0.3 g |
| Dimeralized Water, sufficient quantity for | 100.0 g |
| | 100.0 g |

In addition:  
Titanium dioxide  
Kaolin and Iron  } sufficient quantity for the desired shades  
Oxides

Example XII

Fatty Based Lipstick

A lip stick is prepared according to the following formula:

| Ozokerite | 13.00 g |
|---|---|
| Castor Oil | 35.00 g |
| Hydrogenated Lanolin | 5.00 g |
| Hydrogenated Palm Oil | 5.00 g |
| Oleyl Alcohol | 5.00 g |
| Compound of Example 11 | 21.75 g |
| Isopropyl Lanolate | 10.00 g |
| Liquid Lanolin | 5.00 g |
| B.H.T. (2,6-di-tert-butyl-p-cresol) | 0.1 g |
| Methyl p-hydroxy benzoate | 0.15 g |
| | 100.00 g |

In addition:  
Colorants  
Titanium dioxide  } sufficient quantity for the desired shades  
Mother of Pearl

Example XIII

Semi-Fatty Based Lipstick

A lipstick is prepared according to the following formula:

| Ozokerite | 22 g |
|---|---|
| Liquid Lanolin | 15 g |
| Castor Oil | 22 g |
| Oleyl Alcohol | 10 g |
| Compound of Example 2 | 30.75 g |
| B.H.T. | 0.1 g |
| Methyl p-hydroxybenzoate | 0.15 g |
| | 100.00 g |

In addition:  
Colorants  
Titanium dioxide  } sufficient quantity for the desired shades  
Mother of Pearl

Example XIV

Complexion Cream

A complexion base is prepared according to the following formula:

| | | |
|---|---|---|
| Bees Wax | 9 | g |
| Cetyl Alcohol | 1 | g |
| Cetyl-phosphate of diethanolamine | 0.5 | g |
| Vaseline Oil | 10 | g |
| Compound of Example 2 | 18 | g |
| Borax | 0.8 | g |
| Methyl p-hydroxybenzoate | 0.3 | g |
| Demineralized water, sufficient quantity for | 100 | g |
| | 100 | g |

In addition:
Titanium dioxide
and Iron Oxides  } sufficient quantity for the desired shades
Kaolin

What is claimed is:

1. A bi-substituted derivative of glycerol selected from the group consisting of those of the formula:

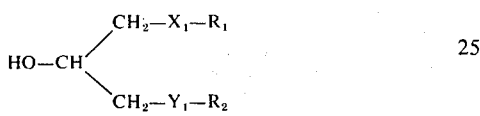

wherein one of the substituents $X_1$ and $Y_1$ is —O— and the other is

$R_1$ is a branched alkyl radical having from 5 to 8 carbon atoms, the number of carbons in the branch being 1, 2 or 3,
and $R_2$ is a linear alkyl radical having from 11 to 18 carbon atoms, and mixtures thereof.

2. A derivative of claim 1 selected from the group consisting of:
dodecanoyloxy-1 (ethyl-2)-hexyloxy-3 propanol-2
octadecanoyloxy-1 (ethyl-2)-hexyloxy-3-propanol-2
dodecyloxy-1 (ethyl-2)-hexanoyloxy-3-propanol-2
octadecyloxy-1 (ethyl-2) hexanoyloxy-3 propanol-2
octadecyloxy-1 (ethyl-2)-butanoyloxy-3 propanol-2 and
tetradecyloxy-1 (ethyl-2)-hexanoyloxy-3 propanol-2
and mixtures thereof.

3. A derivative of claim 1, wherein $R_1$ is

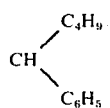

$X_1$ is

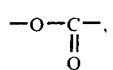

$R_2$ is a mixture of linear alkyl $C_{12}H_{25}$ and $C_{14}H_{29}$, and $Y_1$ is —O—.

4. The derivative of claim 1 wherein the radical $R_1$ is selected from the group consisting of:

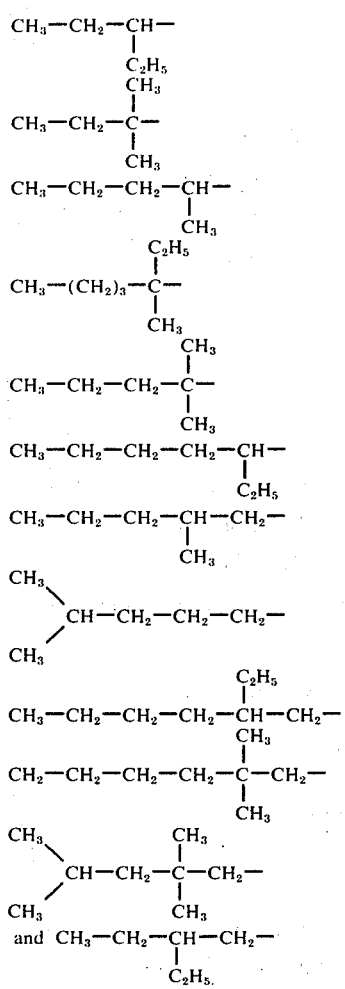

5. The derivative of claim 1 wherein $R_1$ represents either:
a. a radical of the formula:

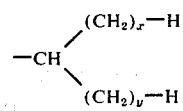

wherein $x$ is 1, 2 or 3, and $y$ is a whole number from 2 to 6, provided that the sum $(x + y)$ is less than or equal to 7, or greater than or equal to 4; or
b. a radical of the formula:

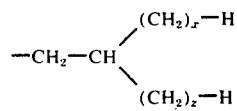

where $x$ is as defined above, and $z$ is a whole number which can vary from 2 to 5, provided that the sum $(x + z)$ is less than or equal to 6, or greater than or equal to 3.

6. The derivative of claim 1 wherein the radical $R_2$ is selected from the group consisting of
$CH_3\text{-}(CH_2)_9\text{-}CH_2\text{-}$,
$CH_3\text{-}(CH_2)_{10}\text{-}CH_2\text{-}$,
$CH_3\text{-}(CH_2)_{11}\text{-}CH_2\text{-}$,
$CH_3\text{-}(CH_2)_{12}\text{-}CH_2\text{-}$,
$CH_3\text{-}(CH_2)_{13}\text{-}CH_2\text{-}$,
$CH_3\text{-}(CH_2)_{14}\text{-}CH_2\text{-}$,
$CH_3\text{-}(CH_2)_{15}\text{-}CH_2\text{-}$, and
$CH_3\text{-}(CH_2)_{16}\text{-}CH_2\text{-}$.

7. The derivative of claim 1 having a viscosity between about 10 cps and 100 cps at 25°C.

* * * * *